United States Patent
Zino et al.

(10) Patent No.: US 9,615,764 B2
(45) Date of Patent: Apr. 11, 2017

(54) REAL-TIME COLORING OF ELECTROPHYSIOLOGICAL MAP

(71) Applicant: BIOSENSE WEBSTER (ISRAEL) LTD., Yokneam (IL)

(72) Inventors: Eliahu Zino, Atlit (IL); Roy Urman, Karkur (IL); Asaf Merschon, Karkur (IL); Shmuel Auerbach, Kerem Maharal (IL); Yaniv Ben Zhriham, Binyamina (IL)

(73) Assignee: BIOSENSE WEBSTER (ISRAEL) LTD, Yokeam (IL)

( * ) Notice: Subject to any disclaimer, the term of this patent is extended or adjusted under 35 U.S.C. 154(b) by 234 days.

(21) Appl. No.: 14/531,130

(22) Filed: Nov. 3, 2014

(65) Prior Publication Data

US 2016/0120427 A1    May 5, 2016

(51) Int. Cl.
*A61B 5/04*     (2006.01)
*A61B 5/044*    (2006.01)
*A61B 5/042*    (2006.01)
*A61B 5/06*     (2006.01)
*A61B 5/0205*   (2006.01)
*A61B 5/00*     (2006.01)
(Continued)

(52) U.S. Cl.
CPC ............ *A61B 5/044* (2013.01); *A61B 5/0084* (2013.01); *A61B 5/02055* (2013.01);
(Continued)

(58) Field of Classification Search
CPC ......... A61B 5/0084; A61B 5/01; A61B 5/015; A61B 5/02055; A61B 5/062; A61B 5/068;
(Continued)

(56) References Cited

U.S. PATENT DOCUMENTS

| 5,738,096 A | 4/1998 | Ben Haim |
| 6,226,542 B1 | 5/2001 | Reisfeld |

(Continued)

FOREIGN PATENT DOCUMENTS

| EP | 1757227 A2 | 2/2007 |
| WO | WO 00/45700 A1 | 8/2000 |
| WO | WO 2012/092016 A1 | 7/2012 |

OTHER PUBLICATIONS

Yokoyama et al, Novel contact force sensor incorporated in irrigated radiofrequency ablation catheter predicts lesion size and incidence of steam pop and thrombus, 2008, Circ. Arrhythm. Electrophysiol. Dec. 2008;1(5):354-62. doi: 10.1161/CIRCEP.108.803650. Epub Dec. 2, 2008.*

(Continued)

*Primary Examiner* — Mallika D Fairchild
(74) *Attorney, Agent, or Firm* — Louis J. Capezzuto

(57) ABSTRACT

Catheterization of the heart is carried out with a probe having a plurality of electrodes and sensors by displaying an electroanatomical map of the heart on a monitor. During a time interval that does not exceed a duration of a cardiac cycle of the heart the following steps are performed: reading data from at least one of the electrodes and sensors, and invoking a processor to perform an algorithm on the data. The data is one of a plurality of inputs of the algorithm, and the result of the algorithm includes a transformation of the data. The method is further carried out by rendering the result of the algorithm on the monitor to modify the electroanatomical map.

21 Claims, 3 Drawing Sheets

(51) Int. Cl.
*A61B 5/11* (2006.01)
*A61B 5/01* (2006.01)

(52) U.S. Cl.
CPC ........ *A61B 5/04012* (2013.01); *A61B 5/0422* (2013.01); *A61B 5/062* (2013.01); *A61B 5/068* (2013.01); *A61B 5/11* (2013.01); *A61B 5/6852* (2013.01); *A61B 5/6869* (2013.01); *A61B 5/6885* (2013.01); *A61B 5/01* (2013.01); *A61B 5/015* (2013.01)

(58) Field of Classification Search
CPC ... A61B 5/04012; A61B 5/0422; A61B 5/044; A61B 5/11; A61B 5/6852; A61B 5/6869; A61B 5/6885
See application file for complete search history.

(56) References Cited

U.S. PATENT DOCUMENTS

| | | |
|---|---|---|
| 6,301,496 B1 | 10/2001 | Reisfeld |
| 6,569,160 B1 | 5/2003 | Goldin et al. |
| 6,814,733 B2 | 11/2004 | Schwartz |
| 6,892,091 B1 | 5/2005 | Ben Haim |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 8,226,580 B2 | 7/2012 | Govari et al. |
| 2004/0039293 A1 | 2/2004 | Porath et al. |
| 2012/0116210 A1 | 5/2012 | Zino |
| 2012/0184858 A1 | 7/2012 | Harlev et al. |
| 2012/0184863 A1 | 7/2012 | Harlev et al. |

OTHER PUBLICATIONS

U.S. Appl. No. 14/166,982, filed Jan. 29, 2014.
U.S. Appl. No. 61/984,953, filed Apr. 28, 2014.
U.S. Appl. No. 14/072,885, filed Nov. 6, 2013.
U.S. Appl. No. 14/132,631, filed Dec. 18, 2013.
U.S. Appl. No. 29/464,664, filed Aug. 20, 2013.
EP15192623 Extended Search Report dated Apr. 4, 2016.

\* cited by examiner

REAL-TIME COLORING OF ELECTROPHYSIOLOGICAL MAP

BACKGROUND OF THE INVENTION

Field of the Invention

This invention relates to cardiac catheterization. More particularly, this invention relates to production of electro-anatomical maps during cardiac catheterization.

Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated to restore the normal function of the heart insofar as is possible.

Mapping of the electrical activation time in the heart muscle requires that the location of the sensor within the heart be known at the time of each measurement. In the past, such mapping was performed using a single movable electrode sensor inside the heart, which sensor measured activation time relative to a fixed external reference electrode. This technique, however, requires calibration, for example impedance calibrations with adjustments for impedance unrelated to that of the body. Mapping of electrical activation time using a single electrode was, furthermore, a lengthy procedure, generally performed under fluoroscopic imaging, and thereby exposing the patient to undesirable ionizing radiation. Furthermore, in an arrhythmic heart, activation times at a single location may change between consecutive beats.

Because of the drawbacks of single-electrode mapping, a number of inventors have taught the use of multiple electrodes to measure electrical potentials simultaneously at different locations in the endocardium, thereby allowing activation time to be mapped more rapidly and conveniently, as described. Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

SUMMARY OF THE INVENTION

Currently data from sensors of various sorts are acquired and accumulated during a catheterization session, and processed as necessary, and after a time represented visually on a monitor, for example as pseudo-colored points or areas on a functional map of the heart. Processing previously captured data in this manner introduces a delay and prolongs the catheterization, as the catheter may need to be repositioned, and the data acquisition steps repeated. According to embodiments of the invention, the data may be visually represented for the operator in near real-time as dynamic modifications of an existing map of the heart as the catheter is moved about or diagnostic maneuvers of various sorts are in progress.

There is provided according to embodiments of the invention a method of catheterization, which is carried out by inserting a probe having a plurality of electrodes and sensors into a heart of a living subject, displaying an electroanatomical map of the heart on a monitor, and during a time interval that does not exceed a duration of a cardiac cycle of the heart, performing the steps of: reading data from at least one of the electrodes and sensors, invoking a processor to perform an algorithm on the data and rendering the result of the algorithm on the monitor to modify the electroanatomical map. The data is one of a plurality of inputs of the algorithm, and the result of the algorithm includes a transformation of the data.

According to a further aspect of the method the algorithm includes selecting first electrodes from the electrodes that are in contact with tissue of the heart, identifying relative motion of the first electrodes with the tissue, selecting second electrodes from the first electrodes, wherein the second electrodes exhibit a predetermined amount of the relative motion, selecting third electrodes from the second electrodes, wherein respective locations of the third electrodes in successive beats have a correlation score below a predetermined threshold, and generating the result from data obtained from the third electrodes.

Yet another aspect of the method includes eliminating data that lies outside a portion of a respiratory cycle prior to generating the result.

According to still another aspect of the method, the time interval does not exceed 500 ms.

According to an additional aspect of the method, the sensors comprise a temperature sensor.

According to still another aspect of the method, the sensors comprise a position sensor.

According to another aspect of the method, the sensors comprise a contact force sensor.

According to a further aspect of the method, the algorithm includes an integration of data from the contact force sensor and position sensors and rendering includes presenting a distorted surface on the electroanatomical map.

According to one aspect of the method, the sensors comprise optical sensors, and the data includes optical reflectance data from the optical sensors. The algorithm includes an analysis of fluctuations in the optical reflectance data and rendering includes displaying an indication of an imminent steam pop event.

According to one aspect of the method, the algorithm includes a calculation of wavefront propagation and rendering includes updating wavefront annotations on the electroanatomical map.

According to another aspect of the method, the algorithm includes a calculation of wavefront propagation and rendering includes updating vectors that represent the wavefront annotations on the electroanatomical map.

According to yet another aspect of the method, the algorithm includes an iterative analysis of temperature data from a plurality of the sensors, and rendering includes displaying an indication of a loss of contact between the probe and a target tissue in the heart.

According to an additional aspect of the method, the electroanatomical map includes an icon image and rendering includes a change in the icon image.

According to another aspect of the method, the electroanatomical map includes regions has boundaries and respective pseudocolors, and rendering includes a change in the boundaries or the pseudocolors.

There is further provided according to embodiments of the invention an apparatus, including a probe having a plurality of electrodes and sensors, electrical circuitry for receiving data from the electrodes and sensors when the probe is at a location in a heart of a living subject, a memory, and a display monitor. A processor is connected to the memory and the display monitor and is operative for displaying an electroanatomical map of the heart on the monitor, and during a time interval that does not exceed a duration of a cardiac cycle of the heart, performing the further steps of reading data from at least one of the electrodes and sensors, and performing an algorithm on the data. The algorithm has a plurality of inputs and a result, wherein the data is one of the inputs and the result includes a transformation of the data. The processor is operative for rendering the result on the monitor to modify the electroanatomical map.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Figure 1:
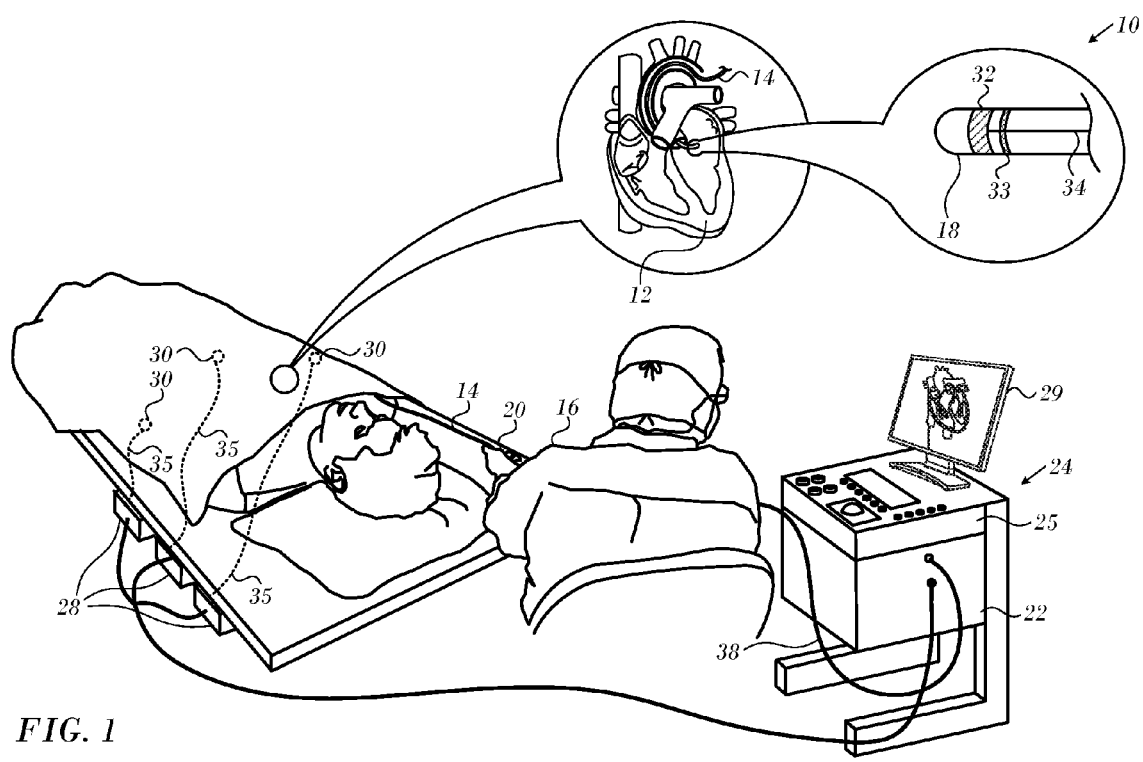
FIG. 1 is a pictorial illustration of a system for performing medical procedures in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultra-sound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images that are described below.

Real-Time Mapping Configuration

Figure 2:
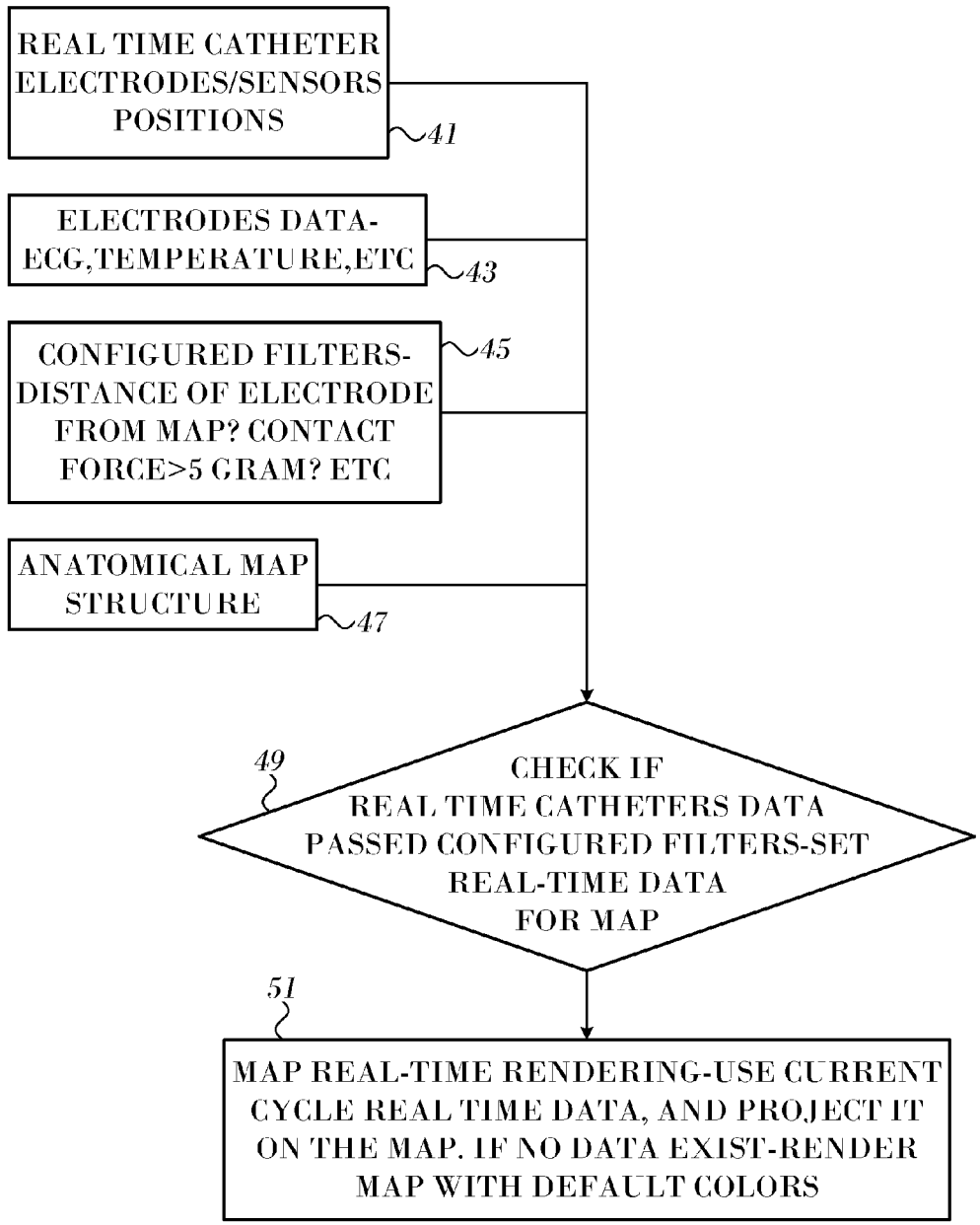
FIG. 2 is a diagram illustrating a configuration of the system shown in FIG. 1 for near real-time data presentation, in accordance with an embodiment of the invention.

Reference is now made to FIG. 2, which is a high level diagram illustrating a configuration of the system 10 (FIG. 1) for near real-time data presentation, in accordance with an embodiment of the invention. For purposes of this disclosure the term "near real-time" refers to processing and presentation in a current cardiac cycle prior to the next cardiac cycle. For example, a typical delay interval between the detection and transmission of a data reading by a sensor and the appearance of a visual representation of the data would be in the order of 500 ms or less. The delay interval could be as short as the cycle length of an arrhythmic focus being evaluated, depending on the resources required for the processor 22 to evaluate the particular data.

The principles of the invention are particularly applicable to data that is not displayed directly on an electroanatomical map, but rather are incorporated in complex algorithms that yield some dynamically changing electrophysiological indicator. The data comprises one input for the algorithm, and is typically one of a plurality of inputs to the algorithm. The outputs of such algorithms are graphically displayed. The outputs of the algorithms are more than a mere depiction of the time and magnitude of the received data, but rather involve some calculation that transforms the data into some electrophysiological indicator by processing the data in combination with other data. The other data also form inputs to the algorithm, and may be currently received, e.g., by other sensors, or may be previously received from the same sensor, other sensors of the same type, sensors of other types, or a combination thereof.

One example is an algorithm for calculating wavefront propagation and updating wavefront annotations on the map that is described in commonly assigned, copending application Ser. No. 14/166,982, entitled Hybrid Bipolar/Unipolar Detection of Activation Wavefront, which is herein incorporated by reference. In this algorithm, a bipolar electrogram and a unipolar electrogram are recorded from electrodes of a probe, and differentiated with respect to time. Peaks are identified in the differentiated bipolar electrogram. An activity window is defined that includes bipolar activity about the peaks. An extreme negative value in the differentiated unipolar electrogram within the activity window is reported as a unipolar activation onset. In one variant, an annotation is selected from candidate minima in the differentiated unipolar electrogram within the activity window by excluding candidates that fail to correlate with activity in the bipolar electrogram.

In another example, the algorithm disclosed in commonly assigned U.S. Patent Application Publication No. 2012/0116210, Visualization of Catheter-Tissue Contact by Map Distortion, which is herein incorporated by reference, integrates data from a surface reflective of contact force sensor and position sensors to present a distorted surface when the force exceeds a predefined amount.

A further example concerns the real-time analysis of optical reflectance data to detect imminent steam pop events during ablation, as disclosed in commonly assigned application Ser. No. 61/984,953, entitled Prevention of Steam Pops during Ablation, which is herein incorporated by reference, in which analysis of high frequency fluctuations in optical reflectivity measured by optical sensors near the tip of a catheter predict an imminent occurrence of steam pops. The analysis may include a Fourier transform of the data or the computation of the second derivative of time-varying data.

Yet another example concerns the repetitive real-time reception of temperature data from a plurality of sensors on an ablation catheter in order to determine loss of contact with target tissue as taught in commonly assigned application Ser. No. 14/072,885, entitled Using Catheter Position and Temperature Measurement to Detect Movement from Ablation Point, and which is herein incorporated by reference.

In all the above examples, data-processing algorithms involve a comparison between currently received data with previously received data in near real-time, or the incorporation of the data as one of a plurality of inputs or parameters for the data-processing algorithm.

Blocks 41, 43, 45, 47 represent types of data that are typically received from a cardiac catheter during a catheterization session. These are presented as examples. Other types of sensors may be read out, for example optical sensors of reflectance data. Block 41 represents input from location sensors that are components of the above-described positioning system. Block 43 represents electrode data and physiologic data from electrodes, e.g., mapping electrodes. Block 43 also includes data from sensors of physical states such as temperature, voltages, electrical phase information, etc. Block 45 concerns filtered or processed versions of raw data, for example, derivations of contact force. Block 47 represents data that represents a current structure of the cardiac chamber or its environment, for example a current reconstruction of the heart from a point cloud of location data as described in commonly assigned, copending application Ser. No. 14/132,631, entitled Dynamic Feature Rich Anatomical Reconstruction from a Point Cloud, which is herein incorporated by reference.

Block 49 is logic that operates continually to determine if data has been received from any of blocks 41, 43, 45, 47. If so the data is classified according its category, special mapping modules are immediately invoked to process the data. While these modules may execute in the processor 22 (FIG. 1), a multi-processor may be employed in order to afford high priority to processing and rendering the data in near real-time.

The results of the processing are rendered to a map display in near real-time in block 51. The rendering may be, for example a change in the color or size of a point on the map, or a change in the pseudocolor of a region of the map, or the boundaries of the region, or a change in a vector. In most cases, the rendering is complete and visible to the operator during the current cardiac cycle. When particularly complex algorithms are involved, delays of up to 500 ms may occur.

In the event that no current data is received in block 49, the special mapping modules are not invoked, and the map is displayed in default colors.

Figure 3:
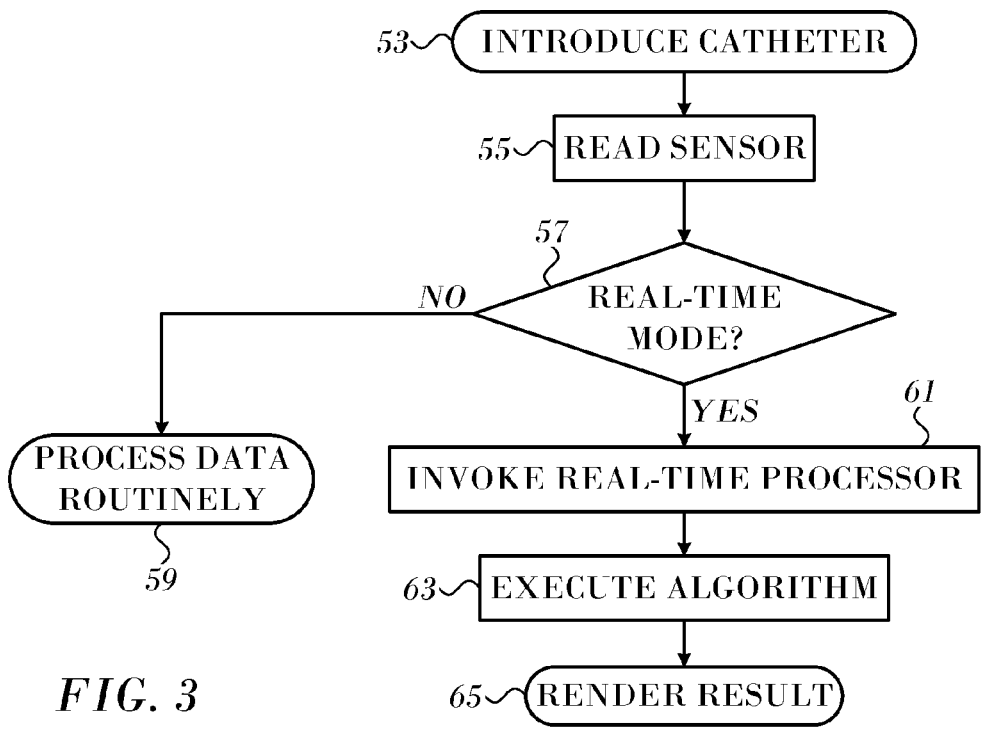
FIG. 3 is a flow-chart of a method for real-time coloring of an electrophysiological map of the heart, in accordance with an embodiment of the invention.

Reference is now made to FIG. 3, which is a flow-chart of a method for real-time coloring of an electrophysiological map of the heart, in accordance with an embodiment of the invention. The process steps are shown in a particular linear sequence in FIG. 3 and the following flow-charts herein for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the process.

At initial step 53, a cardiac catheter is introduced into the heart of a subject using well-known methods.

Next at step 55 one or more sensors on the catheter are read out. The sensors may be any combination of the sensors described in blocks 41, 43, 45 (FIG. 2).

Next, at decision step 57, it is determined if the data received in step 55 is to be processed and displayed on a monitor in near real-time. If the determination is negative, then control proceeds to final step 59. The data is processed conventionally. An update of the display monitor may eventually occur, However the delay interval before the update is visible to the operator generally exceeds the duration of the current cardiac cycle.

If the determination at decision step 57 is affirmative then control proceeds to step 61. A near real-time processor is invoked to perform an algorithm described below, as appropriate for the type of data received in step 55. The processor may be a software process. Alternatively, the processor may be invoked by communicating the data to a hardware processor, a digital signal processor, or hard-wired logic.

At step 63, the near real-time processor executes the selected algorithm using the data received in step 55 as one of its inputs to produce a result. The result is then rendered in final step 65 as a 4-dimensional map, e.g., a movie format. The rendering operation may change a pseudocolor on a portion of the map, move a point, or modify a screen icon such as the animated icon disclosed in commonly assigned Design Application No. 29/464,664 entitled Portion of a Computer Screen with an Icon Image, or the icon disclosed in Design Application No. 29/490874 entitled Enhanced Ablation Site Visualization, the disclosures of which are herein incorporated by reference.

Figure 4:
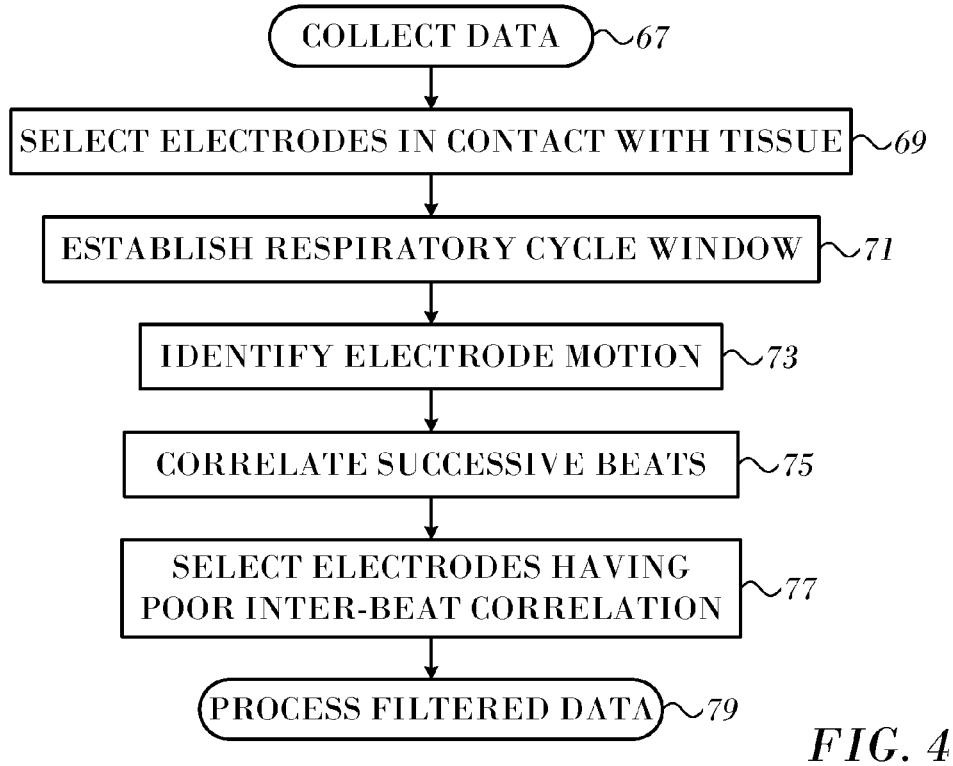
FIG. 4 is a detailed flow chart of aspects of the method shown in FIG. 3.

Reference is now made to FIG. 4, which is a detailed flow-chart describing the algorithm noted in step 63 (FIG. 3), in accordance with an embodiment of the invention. Initial step 67 refers to data collection noted above at step 55.

Next, at step 69 data is selected from electrodes that are in contact with target tissue. Data from electrodes not in contact with tissue are ignored. Electrode contact with tissue can be established by known methods, e.g., from the teachings of U.S. Pat. Nos. 6,569,160 or 8,226,580, the disclosures of which are herein incorporated by reference.

Next, at step 71 a window of the respiratory cycle, e.g., a portion corresponding to end diastole is imposed on the electrode data selected in step 69 and used for further analysis. Data outside this window is ignored.

Next, at step 73 relative motion between the target tissue and the electrodes selected in step 69 is identified respectively. This may be accomplished by many known methods, for example using the location capabilities of the above-noted CARTO system.

Next, at step 75, using the information obtained in step 73, correlation of the electrode locations in successive beats is correlated using well-known correlation methods.

Low correlation scores correspond to positional instability with respect to the target tissue. At step 77, electrodes selected in step 69 undergo further selection, and those having a correlation score below a threshold are chosen.

Having removed large amounts of data in the foregoing steps, the procedure ends at final step 79 the filtered data is now submitted for processing in final step 65 (FIG. 3). The efficiencies achieved by elimination of irrelevant data enables the hardware to process and render the data concurrently with current cardio-respiratory events during the catheterization procedure. The results are perceived by the operator as being current, i.e., in near real-time with no observable delay, and certainly within a current cardiac cycle.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of catheterization, comprising the steps of:
    inserting a probe into a heart of a living subject, the probe having a plurality of electrodes and sensors;
    displaying an electroanatomical map of the heart on a monitor; and
    during a time interval that does not exceed a duration of a cardiac cycle of the heart, performing the further steps of:
    reading data from at least one of the electrodes and sensors;
    invoking a processor to perform an algorithm on the data, the algorithm having a plurality of inputs and a result, wherein the data comprises one of the plurality of inputs and the result comprises a transformation of the data; and
    rendering the result on the monitor to modify the electroanatomical map; and
    wherein the algorithm comprises the steps of:
    selecting first electrodes from the electrodes wherein the first electrodes are in contact with tissue of the heart;
    identifying relative motion of the first electrodes with the tissue;
        selecting second electrodes from the first electrodes, wherein the second electrodes exhibit a predetermined amount of the relative motion;
        selecting third electrodes from the second electrodes, wherein respective locations of the third electrodes in successive beats have a correlation score below a predetermined threshold; and
        generating the result from data obtained from the third electrodes.

2. The method according to claim 1, further comprising the step of eliminating data that lies outside a portion of a respiratory cycle prior to generating the result.

3. The method according to claim 1, wherein the time interval does not exceed 500 ms.

4. The method according to claim 1, wherein the sensors comprise a temperature sensor.

5. The method according to claim 1, wherein the sensors comprise a position sensor.

6. The method according to claim 1, wherein the sensors comprise a contact force sensor.

7. The method according to claim 6, wherein the algorithm comprises an integration of data from the contact force sensor and position sensors and rendering comprises presenting a distorted surface on the electroanatomical map.

8. The method according to claim 1, wherein the sensors comprise optical sensors.

9. The method according to claim 8, wherein the data comprises optical reflectance data from the optical sensors and the algorithm comprises an analysis of fluctuations in the optical reflectance data and rendering comprises displaying an indication of an imminent steam pop event.

10. The method according to claim 1, wherein the algorithm comprises a calculation of wavefront propagation and rendering comprises updating wavefront annotations on the electroanatomical map.

11. The method according to claim 10, wherein the algorithm comprises a calculation of wavefront propagation and rendering comprises updating vectors that representing the wavefront annotations on the electroanatomical map.

12. The method according to claim 1, wherein the algorithm comprises an iterative analysis of temperature data from a plurality of the sensors, and rendering comprises displaying an indication of a loss of contact between the probe and a target tissue in the heart.

13. The method according to claim 1, wherein the electroanatomical map comprises an icon image and rendering comprises a change in the icon image.

14. The method according to claim 1, wherein the electroanatomical map comprises regions having boundaries and respective pseudocolors, and rendering comprises a change in the boundaries or the pseudocolors.

15. An apparatus, comprising:
    a probe having a plurality of electrodes and sensors;
    electrical circuitry for receiving data from the electrodes and sensors when the probe is at a location in a heart of a living subject;
    a memory;
    a display monitor;
    a processor connected to the memory and the display monitor and operative for performing the steps of:
    displaying an electroanatomical map of the heart on the monitor; and
    during a time interval that does not exceed a duration of a cardiac cycle of the heart, performing the further steps of:
    reading data from at least one of the electrodes and sensors;
    performing an algorithm on the data, the algorithm having a plurality of inputs and a result, wherein the data comprises one of the plurality of inputs and the result comprises a transformation of the data; and
    rendering the result on the monitor to modify the electroanatomical map wherein the algorithm comprises the steps of:
    selecting first electrodes from the electrodes wherein the first electrodes are in contact with tissue of the heart;
    identifying relative motion of the first electrodes with the tissue; and
    wherein the algorithm comprises the steps of:
    selecting first electrodes from the electrodes wherein the first electrodes are in contact with tissue of the heart;
    identifying relative motion of the first electrodes with the tissue;
        selecting second electrodes from the first electrodes, wherein the second electrodes exhibit a predetermined amount of the relative motion;
        selecting third electrodes from the second electrodes, wherein respective locations of the third electrodes in successive beats have a correlation score below a predetermined threshold; and
        generating the result from data obtained from the third electrodes.

16. The apparatus according to claim 15, further comprising the step of eliminating data that lies outside a portion of a respiratory cycle prior to generating the result.

17. The apparatus according to claim 15, wherein the time interval does not exceed 500 ms.

18. The apparatus according to claim 15, wherein the sensors comprise a temperature sensor.

19. The apparatus according to claim 15, wherein the sensors comprise a position sensor.

20. The apparatus according to claim 15, wherein the sensors comprise a contact force sensor.

21. The apparatus according to claim 15, wherein the sensors comprise optical sensors.

* * * * *